United States Patent [19]
Redmond et al.

[11] 4,435,174
[45] Mar. 6, 1984

[54] CATHETER GUIDE

[75] Inventors: Russell J. Redmond, Santa Barbara; Donald L. Hannula, Goleta, both of Calif.

[73] Assignee: American Hospital Supply Corporation, Evanston, Ill.

[21] Appl. No.: 367,816

[22] Filed: Apr. 12, 1982

[51] Int. Cl.³ .............................................. A61M 5/00
[52] U.S. Cl. .............................. 604/174; 128/DIG. 26
[58] Field of Search .............................. 604/174–180, 604/DIG. 26

[56] References Cited

U.S. PATENT DOCUMENTS

| | | | |
|---|---|---|---|
| 1,998,225 | 4/1935 | Dow ..................................... | 604/174 |
| 3,722,508 | 3/1973 | Roberts ................... | 128/DIG. 26 X |
| 3,774,616 | 11/1973 | White et al. ............ | 128/DIG. 26 X |
| 3,856,020 | 12/1974 | Kovac .................... | 128/DIG. 26 X |
| 4,164,943 | 9/1979 | Hill et al. ............................ | 604/174 |
| 4,235,234 | 11/1980 | Whitney et al. .................... | 604/177 |
| 4,316,461 | 2/1982 | Marais et al. .......... | 128/DIG. 26 X |

*Primary Examiner*—Stephen C. Pellegrino
*Attorney, Agent, or Firm*—Roger A. Williams

[57] ABSTRACT

A catheter guide is provided which has a base having a first channel extending thereacross for receiving a catheter. An arcuately extending member extends outwardly from the base. A second channel extends along the arcuately extending member for also receiving a catheter. The first and second channels extending respectively across the base and along the arcuately extending member can be enclosed or partially enclosed for retaining a catheter within the channels and within the catheter guide.

13 Claims, 1 Drawing Figure

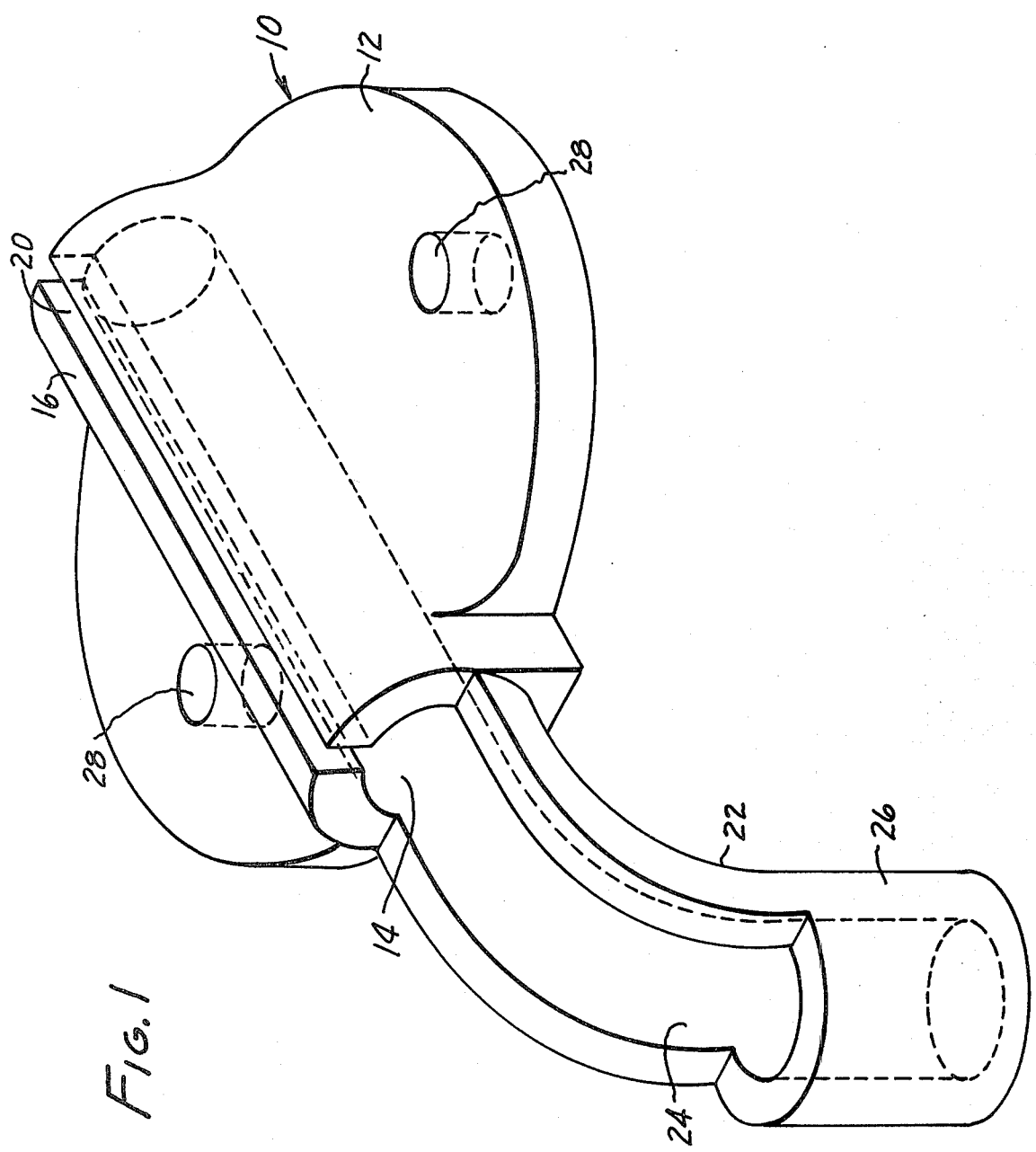

CATHETER GUIDE

BACKGROUND OF THE INVENTION

The invention herein relates to the medical device field and, more particularly, relates to a catheter guide which can be applied to the body or implanted within the body of a patient.

In many instances of patient treatment, it is important to utilize a catheter to direct the flow of body fluids. Depending upon the treatment given to the patient, the catheter can direct the flow of any body fluid. In many instances, it is necessary to direct the flow of the body fluid from one part of the body to another. For example, in the treatment of hydrocephalus, the cerebal spinal fluid (CSF) is directed to either the heart or peritoneal cavity.

During the treatment of a patient, by directing the flow of body fluid, it is in many instances necessary to bend a catheter to direct the flow of the body fluid through the catheter. Such a change in the direction of flow of body fluid is in many instances hampered by the catheter itself through which the body fluid is flowing. Many of the catheters that are utilized are of a resilient material such as a silicone rubber and the like and upon bending, especially at angles of 90° or greater, tend to kink. The kinks that form in the catheter can obstruct or at least inhibit the flow of body fluid through the catheter. When the flow of body fluid is impaired or stopped, the treatment being administered to the patient becomes ineffective, thereby preventing the beneficial treatment to the patient.

SUMMARY OF THE INVENTION

The invention herein is directed to a medical device which can be used in combination with catheters to change the direction of the catheter and thereby the flow of fluid through the catheter without blocking or inhibiting the flow of the fluid through such catheter.

The medical device herein is a catheter guide which can be applied to or implanted within the body of a patient. The catheter guide comprises a base having a catheter receiving channel extending therethrough. The catheter holding channel can be somewhat circular in cross-sectional configuration, at least along a portion of its length, so as to be able to retain a catheter once it is placed within the channel.

Extending from the base is an arcuately extending member. The arcuately extending member has a channel provided therein for receiving the catheter. The channel within the arcuately extending member and the catheter channel extending through the base align for receiving the catheter. The distal end of the arcuately extending member can be provided with an integral element for retaining the catheter within the channel extending along the member.

BRIEF DESCRIPTION OF THE DRAWINGS

These and other features, aspects and advantages of the present invention will be better understood with reference to the appended claims, following description, and accompanying drawing wherein a perspective view of a catheter guide of the invention is shown.

DETAILED DESCRIPTION

The catheter guide herein, which is the subject of the invention, is shown in and will be described with regard to the accompanying drawing. With reference to the drawing, a catheter guide 10 is shown having a base 12. The base is generally flat along on of its surfaces so that it can be placed adjacent a portion of a patient's body.

The catheter guide is preferably made out of a material that is suitable for implanting in the human body. For example, a preferred catheter guide has been constructed from a pliable silicone rubber. Other materials can be used. Barium sulfate can be impregnated within the catheter guide to provide radiopacity to the guide. Other radiopaque materials may be used in place of barium sulfate.

Extending across the base of the catheter guide is a first catheter channel 14. The first channel can have any configuration, depending upon the catheter to be inserted into the guide. As shown in the drawing, the catheter guide is provided with a cylindrical channel for receiving a cylindrical catheter. Along the length of the first channel can be elements for retaining a catheter within the channel. As shown in the drawing of a preferred embodiment, the walls of the channel are generally circular in cross section so as to substantially encircle a catheter placed within the channel. A slot 20 extends along the first channel to provide a pathway for inserting a catheter into the channel. It is not necessary that the side walls of the channel extend to encircle a catheter placed within the channel along the entire length of the first channel.

A member 22 attached to the base extends arcuately outward from the base. The arching configuration of the extending member 22 provides for a change in the direction of a catheter placed within the catheter guide. A second channel 24 is provided within and extending along the arcuately extending member 22. The second channel 24 receives the catheter when it is placed within the catheter guide. Again, as with the first channel, the second channel can have any configuration, depending upon the outer configuration of the catheter to be inserted within the guide.

The arcuately extending member is attached to the base of the catheter so that the first channel in the catheter guide and the second channel in the member align for receiving the catheter. The distal end of the arcuately extending member can be provided with a cylindrical portion for retaining a catheter within the second channel and thereby the catheter guide. The cylindrical portion 26 also can be slotted, if desired, for facilitating the insertion of a catheter. However, in the preferred embodiment, the cylindrical portion is nonslotted, which facilitates retaining the catheter in the angled configuration of the guide. Other structural elements can be provided to the distal end of the arcuately extending member to retain the catheter within the second channel.

To secure the catheter guide to a patient, the guide can be provided with cavities 28 on the base. Such cavities can provide access points for sutures for suturing the catheter guide to a patient. In the preferred configuration of the catheter guide, the cavities 28 are provided on the outwardly extending flanges of the base. The flanges also facilitate upon bending an opening of the slot 20 while inserting a cathete within the base portion of the catheter guide.

A working embodiment of a catheter guide has been constructed and has the following dimensions. The base of the working embodiment of a catheter guide had a length in its longest direction of 0.526 inches and a width of 0.415 inches. The base has a general thickness of about 0.050 inches. The first channel extending across the base was a cylindrical channel having an inside diameter of about 0.086 inches. The slot formed along the base to provide an opening into the first channel had a width of about 0.02 inches. The outwardly and arcuately extending member had a width of about 0.150 inches. The arcuately extending member extended outwardly and downwardly from the base. At the distal end of the arcuately extending member was a cylindrical portion having an opening therethrough with an inside diameter of about 0.103 inches. The outside diameter of the cylindrical portion was 0.150 inches. The center of the cylindrical portion of the arcuately extending member was about 0.200 inches from the base. The distal end of the arcuately extending member terminated approximately 0.225 inches downwardly from the plane of the flat surface of the base. The cavities for suturing the base to a patient were cylindrical and had an inside diameter of 0.040 inches.

The catheter guide can be used to change direction of a catheter. As shown in the drawing, an approximate 90° change in direction can be accomplished using the catheter guide. Other angles can be achieved depending upon the use to which the catheter guide and catheter are being utilized. A catheter once placed in the channels of the catheter guide can follow the channels in the catheter guide around the bend provided by the guide without kinking of the catheter. The flow of body fluid through the catheter is thereby unimpeded and treatment of the patient can continue substantially free of obstructions within the catheter.

As shown, the base of the catheter guide is somewhat oval in cross section. The base has a flat surface for positioning against the patient. Other configurations are contemplated by the invention herein and the configuration of the base is not intended to be limited to the oval shape as shown.

We claim:

1. A catheter guide comprising:
   a base having a channel with a first portion of the channel which extends across the base for receiving a catheter;
   an outwardly and arcuately extending member on the base having a second portion of the channel which extends along such member;
   a first retaining means on the base for retaining a catheter within the first portion of the channel; and
   a second retaining means on the arcuately extending member for retaining such catheter within the second portion of the channel.

2. A catheter guide as recited in claim 1 wherein the first portion of the channel comprises a generally cylindrical cavity extending across the base and wherein a slot extends across the base providing an opening to the cylindrical cavity.

3. A catheter guide as recited in claim 1 wherein the base has a substantially flat surface.

4. A catheter guide as recited in claim 1 wherein the guide is molded with silicone rubber.

5. A catheter guide as recited in claim 4 wherein the catheter guide is impregnated with a radiopaque material.

6. A catheter guide as recited in claim 1 wherein such second retention means comprises a cylindrical end on the arcuately extending member having an opening therethrough for receiving a catheter.

7. A catheter guide as recited in claim 1 wherein the first portion of the channel extending across the base aligns with the second portion of the channel extending along the arcuately extending member.

8. A catheter guide as recited in claim 1 further comprising means on the base for attaching the catheter guide to a patient.

9. A catheter guide as recited in claim 8 wherein such attaching means comprises at least one cavity on the base for providing a suture attachment to the patient.

10. A catheter guide comprising:
    a base having a channel which extends thereacross with a first potion of the channel comprising a generally cylindrical cavity formed in the body including a slot extending across the base and along the cylindrical cavity for providing an opening to the cylindrical cavity and for receiving a catheter in such cylindrical cavity;
    an outwardly and arcuately extending member on the base having a second portion of the channel which extends along such arcuately extending member; and
    a cylindrical end on the arcuately extending member having an opening extending therethrough along the second portion of the channel for receiving a catheter.

11. A catheter guide as recited in claim 10 wherein the guide is molded with silicone rubber.

12. A catheter guide as recited in claim 10 further comprising at least one cavity on the base for providing a suture attachment to the patient.

13. A catheter guide comprising:
    a silicon rubber base having a channel which extends thereacross with a first portion of the channel comprising a generally cylindrical cavity formed in the body including a slot extending across the base and along the cylindrical cavity to provide an opening to the cylindrical cavity and for receiving a catheter in such cylindrical cavity;
    an outwardly and arcuately extending member on the base having a second portion of the channel which extends along such arcuately extending member;
    a cylindrical end on the arcuately extending member having an opening extending therethrough along the second portion of the channel for receiving a catheter; and
    the base including a generally flat side for placement against a portion of a patient's body, which base includes at least one cavity for providing a suture attachment site to the patient.

* * * * *